United States Patent
Ranner et al.

(10) Patent No.: US 8,555,758 B2
(45) Date of Patent: Oct. 15, 2013

(54) METHOD FOR SELECTING AND POSITIONING SEGMENTS OF A KNIFE EDGE

(75) Inventors: Robert Ranner, Vienna (AT); Andreas Loydold, Baden (AT)

(73) Assignee: Leica Mikrosysteme GmbH, Vienna (AT)

( * ) Notice: Subject to any disclaimer, the term of this patent is extended or adjusted under 35 U.S.C. 154(b) by 386 days.

(21) Appl. No.: 12/843,205

(22) Filed: Jul. 26, 2010

(65) Prior Publication Data
US 2011/0067537 A1 Mar. 24, 2011

(30) Foreign Application Priority Data
Jul. 31, 2009 (AT) .................................. 1219/2009

(51) Int. Cl.
*B26D 3/00* (2006.01)
*B26D 5/20* (2006.01)

(52) U.S. Cl.
USPC .................. 83/39; 83/76.1; 83/130; 83/915.5

(58) Field of Classification Search
USPC ........ 83/915.5, 703, 13, 39, 130, 734, 72, 73, 83/74, 76.1, 76.6, 76.8, 76.9
See application file for complete search history.

(56) References Cited

U.S. PATENT DOCUMENTS

| | | | |
|---|---|---|---|
| 5,226,335 A * | 7/1993 | Sitte et al. | 83/74 |
| 5,461,953 A | 10/1995 | McCormick | |
| 6,253,653 B1 * | 7/2001 | Walter et al. | 83/703 |
| 6,634,268 B1 | 10/2003 | Guenther et al. | |
| 7,080,583 B2 * | 7/2006 | Lihl et al. | 83/13 |
| 7,503,248 B2 * | 3/2009 | Studer | 83/703 |
| 8,025,842 B2 * | 9/2011 | Nakajima et al. | 422/65 |
| 8,056,456 B2 * | 11/2011 | Walter | 83/76.8 |
| 8,088,330 B1 * | 1/2012 | Nakajima et al. | 422/65 |
| 2003/0070519 A1 * | 4/2003 | Beld | 83/397 |
| 2003/0101858 A1 * | 6/2003 | Tamura et al. | 83/575 |
| 2004/0107807 A1 * | 6/2004 | Studer | 83/13 |
| 2004/0149106 A1 * | 8/2004 | Hess | 83/575 |
| 2005/0072285 A1 * | 4/2005 | Lang et al. | 83/520 |
| 2006/0248997 A1 * | 11/2006 | Studer | 83/427 |
| 2010/0147120 A1 * | 6/2010 | Walter | 83/13 |

* cited by examiner

*Primary Examiner* — Omar Flores Sanchez
(74) *Attorney, Agent, or Firm* — Hodgson Russ LLP

(57) ABSTRACT

The present invention relates to a method for positioning a cutting knife of a microtome or ultramicrotome equipped with motors for moving the cutting knife. The method may include determining/defining at least two segments of the cutting knife according to a division of the previously defined width of the cutting knife, selecting a segment of the cutting knife, and positioning the cutting knife in an operational position by motorized movement of the cutting knife, the selected segment of the cutting knife being positioned to cut the specimen.

12 Claims, 3 Drawing Sheets

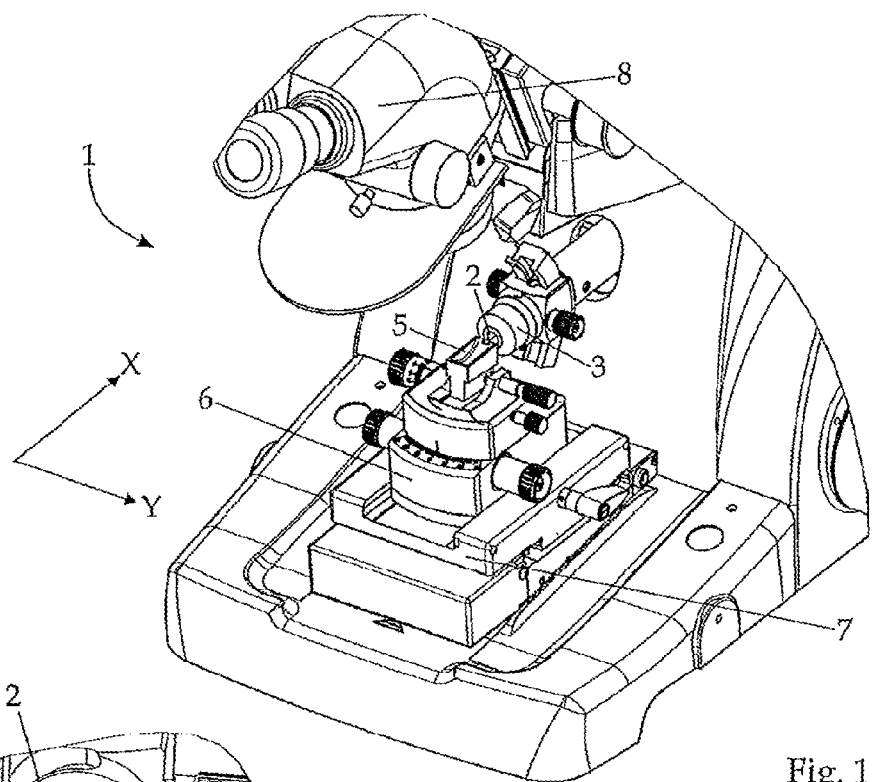
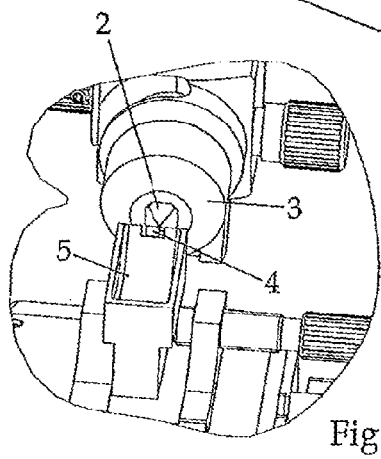
Fig. 2
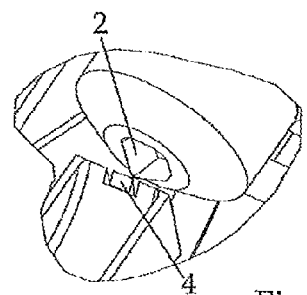
Fig. 3
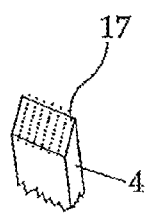
Fig. 4
Fig. 1

METHOD FOR SELECTING AND POSITIONING SEGMENTS OF A KNIFE EDGE

CROSS REFERENCE TO RELATED APPLICATIONS

This application claims priority of the Austrian patent application number 1219/2009 filed Jul. 31, 2009, the entire disclosure of which is incorporated by reference herein.

FIELD OF THE INVENTION

The present invention relates to a method for positioning a cutting knife of a microtome or ultramicrotome equipped with motors for moving the cutting knife.

BACKGROUND OF THE INVENTION

Microtomes are used to prepare very thin specimens, and usually include a knife holder for holding a replaceable knife, and a specimen holder for holding a sample, the sample being moved toward the knife by a feeding mechanism. Ultramicrotomes are used to produce extremely thin sections, such as are used, for example, for transmission electron microscopy. The section thickness is typically in the range from 10 to 500 nm.

Examples of applications include material analysis or examination of soft materials from medical and biological sources. To render the soft materials cuttable, they are embedded in a liquid hardening substance, such as gelatin or synthetic resins.

The replaceable knives used are steel or hard metal knives of different profiles. In ultramicrotomes, glass and diamond knives are used.

The sharpness and hardness of the knives are decisive for a good result and the quality of the sections. Depending on whether hard or soft samples are cut, the knives wear to different degrees. For example, to produce ultrathin sections in an ultramicrotome, expensive diamond knives having cutting edge widths of up to 8 mm are used, the width of wear being within the range of the width of the sample to be sectioned, which is approximately 0.25 mm. When working with a very hard sample, the knife may already be so worn after fewer than ten cuts that proper use is no longer possible.

Therefore, care must be taken to use different portions of the knife edge and to ensure uniform wear of the cutting edge. However, the quality of the knife edge, i.e., the wear thereof, cannot be determined by observation using a stereomicroscope, for example.

Therefore, when using the knives, the user selects a portion for cutting in a more or less arbitrary manner, or switches between such portions during cutting according to his or her subjective assessment. In order not to jeopardize the quality of the sections, knives are frequently replaced with new ones as a precaution. At present, therefore, knives are replaced more or less on speculation, especially if the microtome has not been used for an extended period of time, or if it is used by different users who do not have any information about the wear condition of the knife edge.

This leads to unnecessary costs since knives are replaced or resharpened before the end of their useful lives.

SUMMARY OF THE INVENTION

It is, therefore, an object of the present invention to overcome the above-mentioned disadvantages of the prior art, and to provide a method which allows the quality of the knife to be easily monitored.

According to the method mentioned at the outset, this object is achieved by the following steps:
a) determining at least two segments of the cutting knife according to a division of the previously defined width of the cutting knife;
b) selecting a segment of the cutting knife;
c) positioning the cutting knife in an operational position by motorized movement of the cutting knife, wherein the selected segment of the cutting knife is positioned to cut the specimen.

The method of the present invention allows individual portions of a cutting knife; i.e., the aforementioned segments, to be selected and positioned in a reproducible manner. As a result, the cutting knife wears in a controlled manner. This allows for cost savings since the cutting knife can be fully utilized instead of being prematurely replaced or resharpened on speculation. Generally, at least two segments need to be determined. In practice, however, a significantly greater number of segments may be determined, depending on the width of the cutting knife. Each such segment represents a certain portion of the width of the knife. The segments are directly adjacent to each other.

To enable the selected knife segment to be positioned in a reproducible manner, the knife receptacle, and thus the knife, is movable at least in an east-west direction, said east-west direction being defined relative to the orientation of the knife and substantially parallel to the cutting edge of the knife. A north-south direction is defined such that north is the direction away from the user of the microtome, while south is the direction toward the user (in this regard, see also FIG. 1). According to this definition, and in view of FIG. 1, a movement toward the east corresponds to a movement to the right, while a movement toward the west corresponds to a movement to the left. In principle, the knife receptacle may also be movable in other directions.

The individual steps of the method of the present invention are performed, for example, by means of an adjustment device and/or a control unit of the microtome. The positioning of the selected segment is performed automatically, and not manually by the user.

Advantageously, step a) is performed when an unused cutting knife is inserted, whereas, during the use of the cutting knife, only steps b) and c) are repeated each time a positioning operation is performed. This makes it possible to speed up the method since the segmentation does not change during the use of the knife. When a new knife or a new sample is inserted, segmentation is performed again according to step a) taking into account the width of the new cutting edge (and possibly also the width of the sample).

In a variant of the method according to the present invention, a specified, fixed segment width is used for the division of the cutting knife in step a). This fixed segment width is specified in advance and corresponds, for example, to an average sample width. Hence, the cutting knife is divided into segments in accordance with this specified segment width, regardless of the actual width of the sample (which, however, is smaller than the segment width). Optionally, the position of the sample within the cutting segment may be slightly varied to ensure good utilization of the cutting segment.

In a variant of the method according to the present invention, depending on the type and dimensions of the specimen to be sectioned, the segment width used for the division or segmentation of the cutting knife in step a) corresponds to the actual diameter (i.e., the width) of the specimen to be sectioned. This allows even better utilization of the cutting knife: since the knife wear actually occurring during a cutting operation is only within a width equal to the width of the specimen, the cutting knife can be optimally used over its entire width, using the segments one after another. In this connection, the width of the segment is equal to the width of the specimen within certain tolerances, since the width of the specimen may possibly change in the course of several cutting operations.

In a variant of the present invention, the positioning of the cutting knife in step c) is accomplished by motorized movement in a direction parallel to the cutting edge of the knife. Thus, this movement takes place in the east-west direction described above. This ensures that the selected segment can be properly positioned in a reproducible manner.

Further advantages of the method can be achieved if, when the method is repeated, each selection in step b) is included in the count for each knife segment. Since the selection of a knife segment signifies that the segment is used for cutting, it is thus possible to count the number of cutting operations performed with the respective segment. This allows a direct conclusion to be drawn about the degree of wear of the segment.

In this connection, it is advantageous if the number of times a knife segment is selected is displayed for each segment on a display. As mentioned earlier, the number of selections corresponds to the number of uses, and thus provides information about the degree of wear of the respective knife segment. This makes it possible to obtain information about the degree of wear of a segment prior to selecting it, and, depending on the cutting operation (hard specimen, soft specimen, etc.), a decision can then be made as to whether or not the respective segment is suitable. This is particularly advantageous if the (ultra)microtome has not been used for an extended period of time, of if the same knife is used by different people.

To ensure the reproducibility of the positioning of the cutting knife, the knife is advantageously adjusted to a defined starting position relative to the microtome prior to performing the method. This positioning may be accomplished in various ways, for example, by aligning one end of the cutting knife in a specific way, for example, with respect to a point on the microtome or on the specimen holder. Usually, positioning is carried out such that the right edge of the knife (as viewed in FIG. 1), which defines the first knife segment, is moved into proximity and alignment with the specimen.

Adjustment of the cutting knife to the starting position may be done manually using a stereomicroscope. This means that the cutting knife, or knife holder, is moved by hand (i.e., that the motors for movement in the east-west direction are controlled by the user) while monitoring the instantaneous position of the knife through the stereomicroscope. This allows for optimum positioning.

In an advantageous variant of the invention, method steps a) and b) are controlled by a user via a graphical software interface, using a representation of the division of the cutting knife into knife segments and of the number of selections made per knife segment in step a), and a representation of the knife segments selectable in step b).

BRIEF DESCRIPTION OF THE DRAWING VIEWS

The present invention will now be explained in more detail with reference to a non-limiting exemplary embodiment schematically illustrated in the drawing, in which:

FIG. 1 is a partial view of an ultramicrotome;

FIG. 2 is a partial view of the knife/specimen area of an ultramicrotome such as that shown in FIG. 1;

FIG. 3 is a detail view showing the cutting knife and specimen of FIG. 2;

FIG. 4 is a schematic view of a segmented cutting knife;

DETAILED DESCRIPTION OF THE INVENTION

Figure 5:
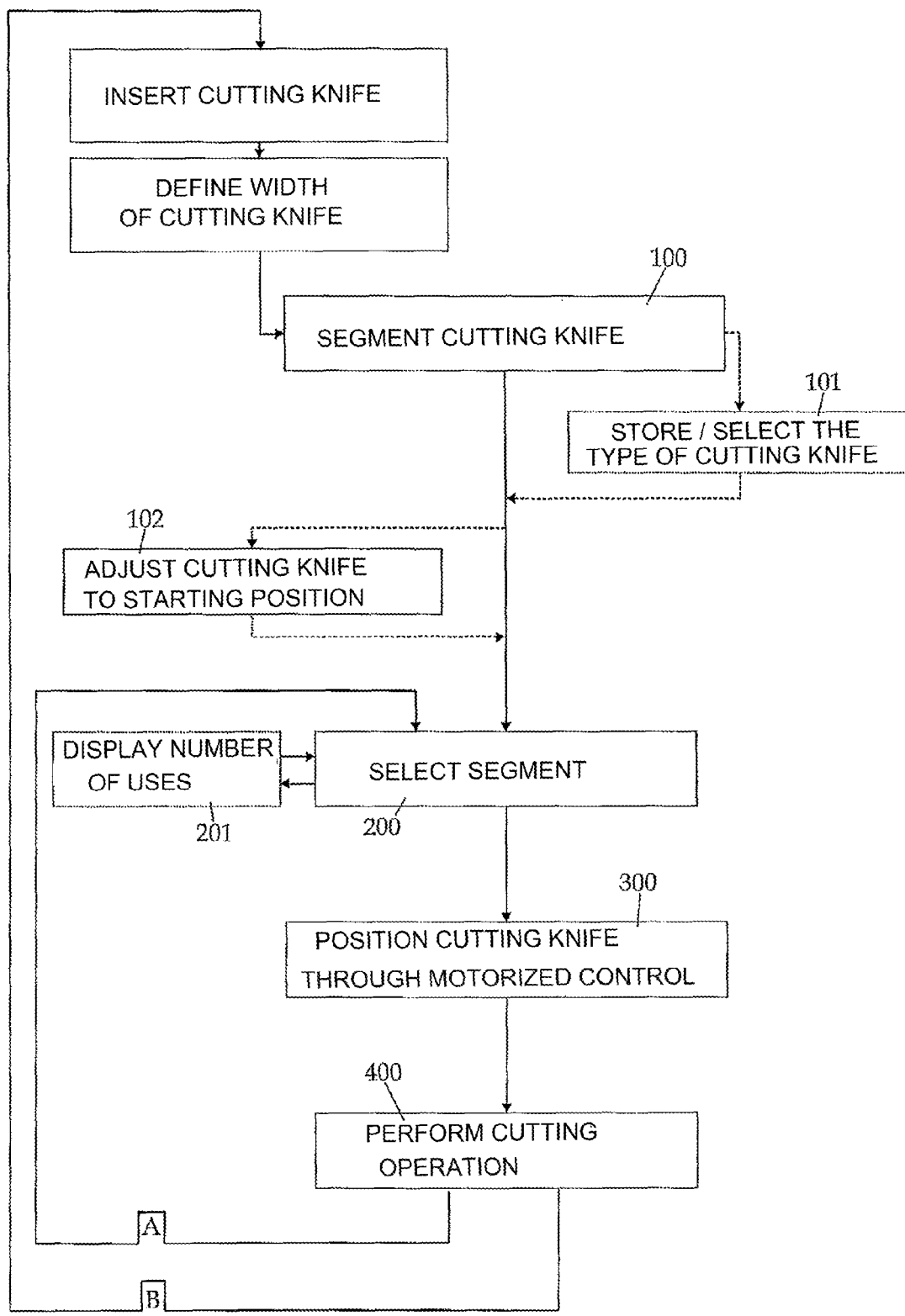
FIG. 5 is a flow chart of the method according to the present invention.

The method according to the present invention finds application, for example, in an ultramicrotome such as that shown in FIGS. 1 through 3.

FIG. 1 shows, in a partial view, the knife/specimen area of an ultramicrotome 1. A stereomicroscope 8 (partially shown in FIG. 1) is provided to allow observation of the knife/specimen area. A specimen 2 is fixedly disposed in a specimen holder 3. The specimen may be one of various types of samples, including biological specimens, such as tissue samples, materials from medical or biological sources, as well as plastics.

In the present example, the cutting knife used is a diamond blade 4 (see FIG. 2). Generally, hard metal or steel knives are used in microtomes, while diamond and glass knives are used in ultramicrotomes to produce particularly fine sections. In order to prevent damage to diamond blade 4, it is preferred to produce only sections having a maximum thickness of 1 μm.

Diamond blade 4 is disposed in a knife trough 5 and fixed in a known manner by a suitable holding device; i.e., in a knife receptacle (not shown in FIG. 1). Knife trough 5 is disposed on a rotatable knife holder 6, which in turn is clamped to an x/y stage 7. The x- and y-directions are as indicated by the axis system shown. Accordingly, the x-axis extends in the north-south direction, while the y-axis extends in the east-west direction. These designations are based on the arrangement shown in FIG. 1.

Mobility in both directions is necessary to move diamond blade 4 into precise alignment and close proximity with specimen 2, in particular before the cutting operation is started.

Knife trough 5 is filled with water for the cutting operation. The thin sections produced during the cutting operation float on the water surface and can be collected using a support grid, such as is used in electron microscopy. The configuration shown in FIG. 1 is only one of several possible configurations. In low-temperature applications, knife trough 5 is omitted and the sections are placed dry on the support grids using manipulators.

FIG. 2 shows a partial view of the knife/specimen area of FIG. 1. Diamond blade 4 is in proximity and alignment with specimen 2, which is mounted in specimen holder 3. This means that diamond blade 4 does not touch specimen 2, but is merely positionally adjusted with respect thereto. Contact occurs only during the cutting operation. The arrangement of diamond blade 4 within knife trough 5 is shown in this figure.

Specimen 2 is in the shape of a pyramid having a truncated apex (see FIG. 3). This truncated apex is the surface from which sections are cut using diamond blade 4. As can be clearly seen in FIG. 3, the cut surface of specimen 2 is much smaller than the width of diamond blade 4. Therefore, in order to always obtain optimum cutting action of diamond blade 4, advantageously, a different portion of the width of diamond blade 4 is used for each cutting operation.

In prior art approaches, diamond blade 4 is manually aligned with respect to the specimen. In the process, a blade portion is selected and positioned, as it were, on a hit-or-miss basis. In particular, if the ultramicrotome (or the knife) is used by different people or has not been used for an extended period of time, the condition of diamond blade 4 is unclear. Therefore, in order not to jeopardize the quality of the sections, the blade will be replaced or resharpened on speculation.

In contrast, in the method of the present invention, diamond blade 4 is positioned with respect to the specimen in a controlled manner. This positioning is preferably done by means of an adjustment device of microtome 1 and/or a control unit. User control is facilitated by a graphical software interface via a computer. A screenshot of the aforementioned software interface is shown, by way of example, in FIG. 6 and described further below.

The essential steps of the method are illustrated in a flow chart in FIG. 5. The method starts with the insertion of a new (i.e.; unused or newly sharpened) cutting knife into microtome 1, for example, into a holding device of generally known type in knife trough 5. This knife may be a diamond blade 4 as described above, but it may also be a different kind of knife. Therefore, in the description of FIG. 5, the term "cutting knife" is used in a general, non-limiting sense.

When using a software interface such as mentioned above, the insertion of the cutting knife is followed by entering the width of the knife (i.e., of its cutting edge). The width of the cutting knife is always defined in this step. If it is unknown, it is determined, for example, by measurement.

This is basically followed by three fundamental steps:
Step 100: determining at least two segments of the cutting knife according to a division of the previously defined width of the cutting knife;
Step 200: selecting a segment of the cutting knife;
Step 300: positioning the cutting knife in an operational position by motorized movement of the cutting knife, wherein the selected segment of the cutting knife is positioned to cut the specimen.

In step 100, the width of the cutting knife is divided into a number of segments. The width of the segments may be selected in various ways. In a first variant, the width of the segments, and thus the number of segments per cutting knife, is determined according to the width of the specimen. Thus, the width of the segment is identical to the width of the specimen. In a second variant, a fixed segment width is specified. In this case, the width of the cutting knife is divided into segments having the specified width, regardless of the width of the particular specimen to be sectioned. The specified width may be, for example, the typical average width of a specimen.

Thus, a segment is a specific portion of the width of the knife edge, and the segments are immediately adjacent to each other. When using a software interface, the segmentation is done by this interface, or according to the division of the width of the knife edge into segments.

The division into segments is schematically illustrated in FIG. 4: A diamond blade 4, such as is shown in FIGS. 1 through 3, is divided into seven segments. Then, to facilitate handling, a first segment is defined and used as a starting point for the counting of the other segments (of course, the individual segments may be designated not only by numbers, but also by letters or other combinations of characters). In the present case, the count starts from the right side (as viewed in FIG. 4); i.e., the first segment is the one on the very right and is denoted by reference numeral 17. The boundaries of the segments are indicated by dotted lines. As mentioned earlier, it is, of course, possible to make a division into a number of segments greater or less than that shown, the condition being that at least two segments are provided.

In an optional intermediate step,
Step 101: store or select the type of cutting knife,
the segmentation can be associated with the knife and stored or selected, respectively. In the process, it is possible to store, for example, a kind or a type of knife, so that each time a cutting knife of the same kind or type is used again, it is then no longer necessary to determine the segmentation, but simply to select the correct kind of knife. For example, when inserting a new cutting knife of a kind that has been used before, step 100 will be omitted and the stored kind of knife will be retrieved along with the segmentation information in step 101. This further simplifies the operation through management of various kinds or types of knifes. This knife data is stored in a database of known kind.

In a further optional intermediate step,
Step 102: adjust the cutting knife to a starting position,
the knife is moved into a starting position. This starting position is defined relative to the microtome or the specimen. For example, the left or right end of the cutting knife is positioned relative to a point on microtome 1 or relative to the specimen.

A possible variant would be to adjust the right edge of the cutting knife relative to the specimen and to define the right outer segment as the first segment, as mentioned in the description of FIG. 4.

Adjustment of the cutting knife may, for example, be done manually, by moving knife holder 6 and x/y stage 7, either manually or by motorized means. This adjustment operation is performed with the aid stereomicroscope 8 (FIG. 1).

The positions of steps 101 and 102 in the flow chart of FIG. 5 represent one of several options. The steps may also be carried out in reverse order, or at other suitable points within the process. Although the method of the present invention includes the adjustment of the cutting knife to a starting position as an optional step, it will be useful to carry out such a step prior to starting a cutting operation with a new cutting knife.

The selection of a segment in step 200 may be done, for example, by selecting a segment in the graphical software interface, which ideally shows a schematic representation of the segmented cutting knife. The selection of a segment is then done, for example, by clicking on it or entering a letter or number code associated with the segment. In the same way, it is also possible to switch between segments.

In an optional intermediate step,
Step 201: display the number of selections per knife segment,
the number of times the respective knife segments have already been used for cutting operations is indicated on a display (for example, of a graphical user interface) during segment selection. To this end, each selection made in step 200 is recorded in a memory. Knowing the properties of the sample (hard, soft) and the kind and type of the cutting knife, the user can then decide which segment is suitable for the cutting operation, or whether the cutting knife needs to be replaced. Thus, even if there are longer intervals between cutting operations, or if the microtome is used by different people, it is advantageously possible to obtain clear information about the condition; i.e., the degree of wear, of the cutting knife.

In step 300, the selected segment is then positioned through motorized, automatic control. If the cutting knife is in a correct starting position, the cutting edge is reproducibly positioned relative to the specimen by motorized movement in the y-direction (i.e., in the east-west direction, a direction parallel to the cutting edge). If, as described in step 100, a fixed segment width is specified which is wider than the width of the specimen, the respective segment can then be adjusted more accurately relative to the specimen. Thus, initially, the selected segment is positioned, and then a fine adjustment may be made within the segment, for example by manual control of motorized movable x/y stage 7 (FIG. 1).

In a further step,

Step 400: perform cutting operation, the cutting operation is then carried out. Steps 200 through 400, including the optional intermediate steps, may be repeated any number of times until replacement of the cutting knife required. The preceding steps must, in principle, be carried out only once when a new cutting knife is inserted. Theoretically, of course, they may also be carried out each time a new cutting operation is performed.

Quite generally, therefore, upon completion of the cutting operation, it is possible to either initiate step 200 again (variant A in FIG. 5) or, if a new cutting knife is needed, to restart with the insertion of the cutting edge (variant B in FIG. 5).

Figure 6:
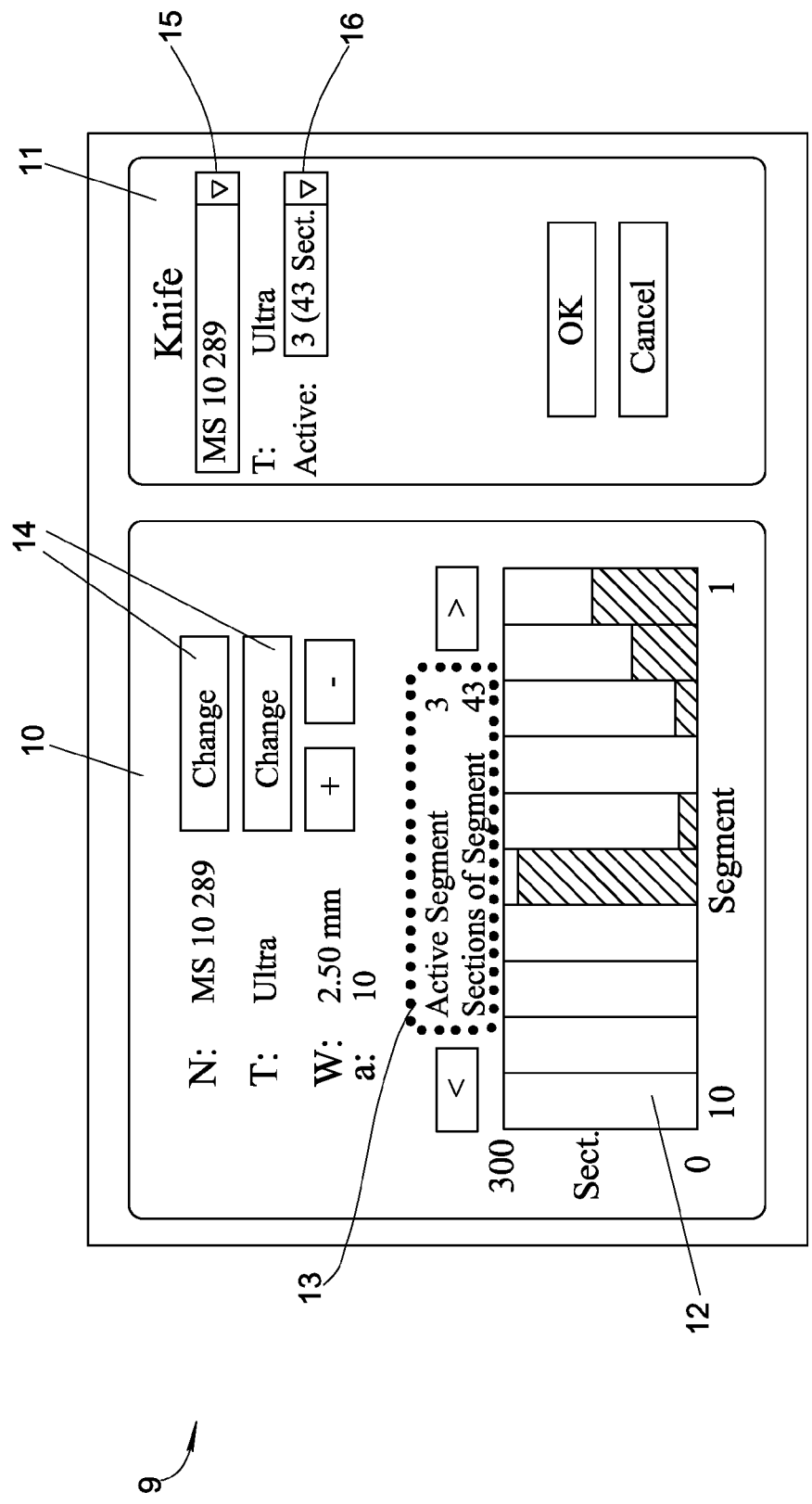
FIG. 6 is a schematic view of a graphical user interface for carrying out the method of the present invention.

Advantageously, the respective method steps can be controlled by a user via a graphical software interface. An exemplary user interface 9 is shown in FIG. 6. This user interface 9 has two portions 10, 11, namely a left portion 10 and a right portion 11.

A display area 12 in left portion 10 presents the segments of the cutting knife (or of diamond blade 4) on the abscissa. In the present case, there are ten segments. The ordinate shows the number of uses (i.e., the number of selections, and thus also of cutting operations) per segment. The designation "Sect." refers to the sectioning or cutting operations, which are represented in the form of bars above the segment numbers. In a region 13 located above display area 12 and marked by a dotted box are displayed the number of the currently used segment ("Active Segment") and the number of sections made by the segment ("Sections of Segment").

The kind or name ("N") and the type ("T") of the knife, and the width ("W") of the cutting edge of the particular kind of knife are displayed in the upper part of left portion 10. In this connection, it is also possible to change the segmentation; i.e., the number of segments ("S") (This option does not apply in cases where a fixed segment width is specified, as described above in step 100). If the kind of knife is to be changed, the right portion 11 of user interface 9 entitled "Knife" may be activated by actuating the "Change" control button 14.

In this manner, the kind and type of knife can be changed. The kind of knife is selected from a first menu 15, while the active segment ("Active") can be selected via a second menu 16.

Additional kinds of knives can be entered via an input mask of known kind, the individual knife types and their number of uses being stored in a suitable memory.

What is claimed is:

1. A method for positioning a cutting knife of a microtome or ultramicrotome equipped with motors for moving the cutting knife, the method comprising the steps of:
    a) determining at least two segments of the cutting knife according to a division of a width of the cutting knife;
    b) selecting one of the at least two segments of the cutting knife; and
    c) positioning the cutting knife in an operational position by motorized movement of the cutting knife, wherein the selected segment of the cutting knife is positioned to cut the specimen;
    d) storing a count for each of the at least two segments indicating the number of times the corresponding segment has been selected.

2. The method as recited in claim 1, further comprising the step of displaying the count for each of the at least two segments on a display.

3. The method as recited in claim 2, wherein the method steps a) and b) are controlled by a user via a graphical software interface, the interface including a representation of the division of the cutting knife into knife segments and of the count for each of the at least two segments, and a representation of the knife segments selectable in step b).

4. The method as recited in claim 3, wherein the interface displays one or more of the following: name of the cutting knife, type of the cutting knife, and width of a cutting edge of the cutting knife.

5. The method as recited in claim 4, wherein the interface includes a change control for changing the name of the cutting knife, the type of the cutting knife, or the width of the cutting edge of the cutting knife.

6. The method as recited in claim 1, wherein the cutting knife is a diamond blade.

7. The method as recited in claim 1, wherein step a) is performed when an unused cutting knife is inserted in the microtome or ultramicrotome, whereas, during the use of the cutting knife, only steps b) and c) are repeated.

8. The method as recited in claim 1, wherein a specified, fixed segment width is used for the division of the cutting knife width in step a).

9. The method as recited in claim 1, wherein a segment width used for the division of the cutting knife width in step a) corresponds to a width of a specimen to be sectioned.

10. The method as recited in claim 1, wherein the positioning of the selected segment in step c) is accomplished by motorized movement of the cutting knife in a direction parallel to a cutting edge of the cutting knife.

11. The method as recited in claim 1, further comprising a preliminary step of adjusting the cutting knife to a defined starting position relative to the microtome or ultramicrotome.

12. The method as recited in claim 11, wherein adjustment of the cutting knife to the starting position is done manually with the aid of a stereomicroscope.

* * * * *